United States Patent [19]

Brown

[11] Patent Number: Plant 6,857

[45] Date of Patent: Jun. 13, 1989

[54] AGLAONEMA 'B.J. FREEMAN'

[75] Inventor: B. Frank Brown, Palm Bay, Fla.

[73] Assignee: Weyerhaeuser Company, Tacoma, Wash.

[21] Appl. No.: 153,733

[22] Filed: Feb. 8, 1988

[51] Int. Cl.[4] ..... A01H 5/00
[52] U.S. Cl. ..... Plt./88
[58] Field of Search ..... Plt./88

[56] References Cited

PUBLICATIONS

Bailey, L. H. & E. Z., 1976, *Hortus Third,* Macmillian, N.Y.

Graf, A. B., 1978, *Tropica — Color Cyclopedia of Exotic Plants and Trees,* Rohers Co., East Rutherford, N.J.

Jervis, R. N., 1987, *Florida Ornamental Plants, Aglaonema Growers Notebook,* Clearwater, Fla.

*Primary Examiner*—Robert E. Bagwill

[57] ABSTRACT

A new and distinct variety of Aglaonema having a full and compact appearance, a vigorous growth rate and an upright and spreading habit. The large stature resembles Dieffenbachia species. Leaves are large and variegated with two distinct colors on the upper surface. The basic leaf color is a glaucous-appearing silvery-green with dark green margins. The area next to the margins and the midrib have blotches and spots of the same color as the margins.

2 Drawing Sheets

The present invention relates to a new and distinct hybrid of Aglaonema commonly known as "Chinese Evergreen" in the Araceae family.

This new variety of Aglaonema originated as a seedling selection of *Aglaonema crispum* (Hort. Pitcher & Manda) Nicols. [*A. roebelinii,* Hort. Pitcher & Manda; *Schismatoglottis roebelinii* (Hort. Pitcher & Manda) Hort. Pitcher & Manda], commonly known as "Painted Drop-Tongue." This new variety was selected because of its unique characteristics. It was discovered and isolated and has been grown in a shade house in Valkaria, Fla. The new selection has been reproduced numerous times at the Weyerhaeuser Tissue Culture Center, Apopka, Fla. by asexual propagation (divisions and cuttings). Each of the progeny exhibits identical characteristics to the new selection, establishing this plant as reproducable and true to type.

This new Aglaonema selection has many desirable and distinctive traits which render it unique from any other varieties of Aglaonema commercially available. It is also unlike any of those described by Graf, Bailey, or Jarvis (see list of references) as evidenced by the following combinations of characteristics:

(1) A robust suckering habit (develops many lateral offsets) which gives the plant a full and compact appearance. The plant also has a vigorous growth rate, an upright and spreading habit, and a large stature that resembles Dieffenbachia species.

(2) The large elliptic leaves are uniquely variegated with two distinct colors on the upper leaf surface. The basic color of the upper leaf surface is a silvery-green with a glaucous appearance (although the surface is not glaucous). The leaf margins are edged in dark green about 6 mm (¼ in) wide around the entire leaf circumference. The area next to the margins (also the same color) has blotches and spots in irregular patterns. The midrib area has sporadic blotches, streaks and spots (the same color as the margins and other blotches).

BRIEF DESCRIPTION OF THE PHOTOGRAPHS

DETAILED PLANT DESCRIPTION

Figure 1:
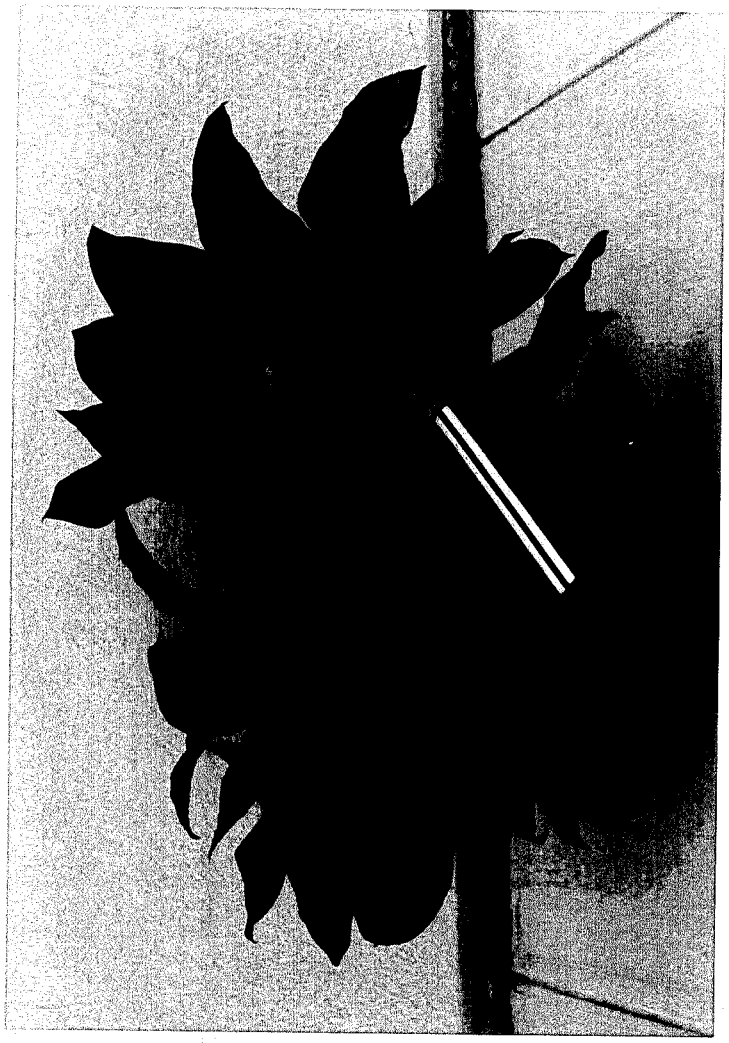
FIG. 1 shows an unpruned individual plant demonstrating the overall size and growth pattern, the robust suckering habit, and the compactness and large spreading stature.
Figure 2:
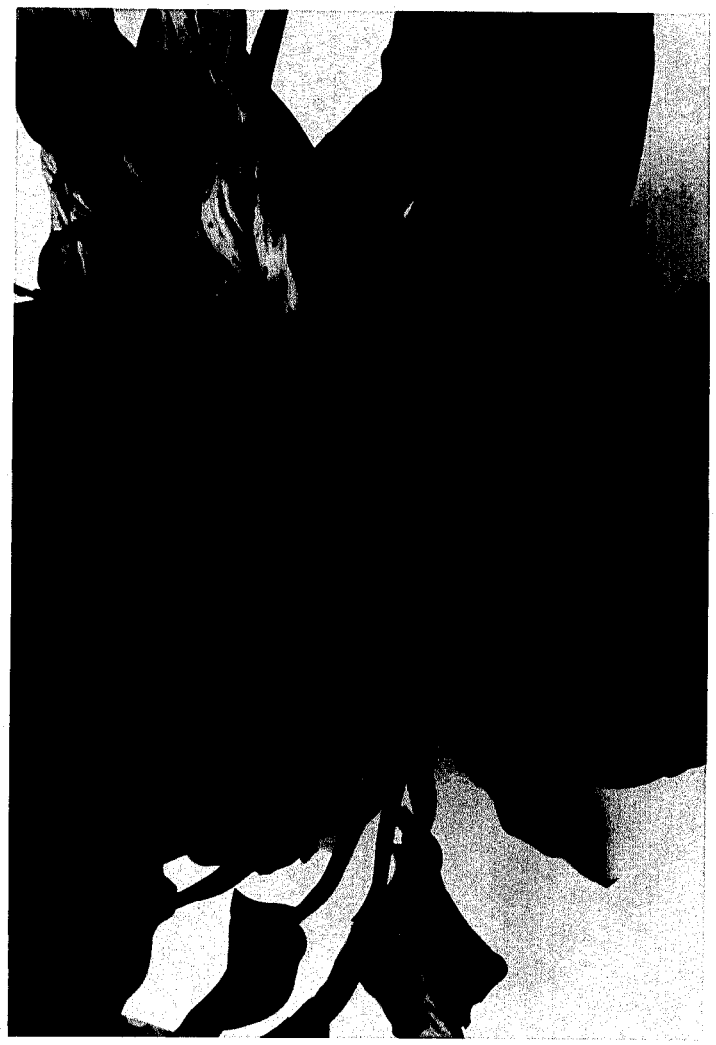
FIG. 2 is a closeup view showing the unique color and mottling pattern of the upper leaf surfaces and the essentially unvariegated color of the lower leaf surfaces.

The following is a detailed description of the new Aglaonema plant based on observations of specimen plants grown in Apopka, Fla. The color determinations and comparisons are all based on The Royal Horticultural Society Colour Chart.

Overall size and growth habit: Present indications are that the height will range up to about 6 feet and about 3 feet wide. The growth habit is compact, upright, ascending and spreading. The plant suckers freely (develops many lateral offsets) and has grown between 15.2 cm to 20.3 cm (6 to 8 in) per year.

Foliage:

*Type.*—Herbaceous, evergreen.
*Shape.*—Elliptic.
*Texture.*—Glabrous.
*Length.*—27.9 cm to 38.1 cm (11 to 15 in).
*Width.*—11.4 cm to 16.5 cm (4½ to 6½ in).
*Petiole length.*—12.7 cm to 17.8 cm (5 to 7 in).
*Margins.*—Entire, moderately undulate.
*Base.*—Rounded to oblique.
*Apex.*—Broadly acuminate, twisted or recurved.
*Leaf arrangement.*—Alternate.
*Venation.*—Pinnate, sunken midrib and veins.

Color characteristics:

*Mature leaves upper surface.*—Leaf color — (basic coloration) R.H.S. Colour Chart Fan 3, Green Group, No. 138 C. Blotches, streaks and spots — R.H.S. Colour Chart Fan 3, Green group, No. 137 A. Margin — R.H.S. Colour Chart Fan 3, Green Group, No. 137 A. Midrib area — R.H.S.

Colour Chart Fan 3, Green Group, 137 A. Lower leaf surface — R.H.S. Colour Chart Fan 3, Yellow-Green Group, No. 146 B. Petioles — R.H.S. Colour Chart Fan 3, Yellow-Green Group, No. 146 B.

*Newly emerging leaves upper surface.*—Leaf color — (basic coloration) R.H.S. Colour Chart Fan 3, Yellow-Green Group, No. 146 C. Blotches, streaks and spots — R.H.S. Colour Chart Fan 3, Yellow-Green Group, No. 146 A.

Descriptions and Differences of Parent Plant

*Aglaonema crispum* (painted drop-tongue):

*Leaf shape.*—Elliptic, similar to the new selection.

*Leaf length.*—To 30.5 cm (12 in), not as large as the new selection.

*Leaf width.*—To 14 cm (5½ in), not as wide as the new selection.

*Petioles.*—To 20.3 cm (8 in), green with paler blotches, similar to the new selection.

*Leaf color.*—Dark olive green with a large irregular overlay pattern of silvery grey-green which fills most of each half of the blade. The colors are similar to that of the new selection but the variegation patterns are not. The new Aglaonema variety does not have as much dark green in the midrib area as *A. crispum.*

References

Bailey, L. H. & E. Z., 1976. *Hortus Third,* Macmillan, N.Y.

Brown, B. F., 1980. New discoveries, new hybrids, and related knowledge. *Aroideana,* Publication of the International Aroid Society 3(4): 120–126.

Brown, B. F., 1984. The new Aglaonemas of Thailand. *Aroideana* 7(2): 43–52.

Graf, A. B., 1978. *Tropica — Color cyclopedia of Exotic Plants and Trees.* Roehrs Co., East Rutherford, N.J.

Jervis, R. N., 1987. *Florida Ornamental Plants, Aglaonema Growers Notebook.* Clearwater, Fla.

I claim:

1. A new and distinct variety of Aglaonema substantially as shown and described, characterized by:

a full and compact appearance, a vigorous growth rate and an upright and spreading habit, and a large stature that resembles Dieffenbachia species;

the variety further having large elliptic leaves variegated with two distinct colors on the upper leaf surface, the basic color being a silvery-green with a glaucous appearance, with dark green leaf margins around the entire circumference, the area next to the margins and the midrib having blotches and spots of the same color as the margins.

* * * * *